(12) United States Patent
Quake et al.

(10) Patent No.: US 8,932,461 B2
(45) Date of Patent: Jan. 13, 2015

(54) MICROFLUIDIC SIEVE VALVES

(75) Inventors: Stephen R. Quake, Stanford, CA (US); Joshua S. Marcus, Altadena, CA (US); Carl L. Hansen, Vancouver (CA)

(73) Assignee: California Institute of Technology, Pasadena, CA (US)

( * ) Notice: Subject to any disclaimer, the term of this patent is extended or adjusted under 35 U.S.C. 154(b) by 782 days.

(21) Appl. No.: 13/171,329

(22) Filed: Jun. 28, 2011

(65) Prior Publication Data

US 2012/0061305 A1    Mar. 15, 2012

Related U.S. Application Data

(62) Division of application No. 11/792,170, filed as application No. PCT/US2005/043833 on Dec. 5, 2005, now abandoned.

(60) Provisional application No. 60/633,121, filed on Dec. 3, 2004.

(51) Int. Cl.
    *B01J 20/28* (2006.01)
    *B01J 20/286* (2006.01)
    (Continued)

(52) U.S. Cl.
    CPC ........... *B01J 20/286* (2013.01); *F16K 99/0001* (2013.01); *F16K 99/0026* (2013.01); *F16K 99/0059* (2013.01); *G01N 30/6004* (2013.01); *B01J 2220/54* (2013.01); *F16K 99/0034* (2013.01); *F16K 2099/0074* (2013.01); *F16K 2099/008* (2013.01); *F16K 2099/0084* (2013.01); *G01N 30/603* (2013.01); *G01N 30/6095* (2013.01)

USPC .......................................... 210/198.2; 210/656

(58) Field of Classification Search
    CPC . B01J 20/286; B01J 2220/54; F16K 99/0001; F16K 99/0026; F16K 99/0059; F16K 99/0034; F16K 2099/0074; F16K 2099/008; F16K 2099/0084; G01N 30/6004; G01N 30/6095; G01N 30/603
    USPC ....................................... 210/656, 198.2, 418
    See application file for complete search history.

(56) References Cited

U.S. PATENT DOCUMENTS 6,408,878 B2    6/2002    Unger et al.
6,540,895 B1    4/2003    Spence et al.
(Continued)

FOREIGN PATENT DOCUMENTS

WO    WO 01/01025 A2    1/2001
WO    WO 01/67369 A2    9/2001
(Continued)

OTHER PUBLICATIONS

Chou et al., "A Microfabricated Rotary Pump" *Biomedical Microdevices* 3:323-330 (2001).
(Continued)

*Primary Examiner* — Ernest G Therkorn
(74) *Attorney, Agent, or Firm* — Kilpatrick Townsend & Stockton LLP (57) ABSTRACT

Sieve valves for use in microfluidic device are provided. The valves are useful for impeding the flow of particles, such as chromatography beads or cells, in a microfluidic channel while allowing liquid solution to pass through the valve. The valves find particular use in making microfluidic chromatography modules.

20 Claims, 5 Drawing Sheets

(51) Int. Cl.
*F16K 99/00* (2006.01)
*G01N 30/60* (2006.01)

(56) References Cited

U.S. PATENT DOCUMENTS

| | | |
|---|---|---|
| 6,752,922 B2 | 6/2004 | Huang et al. |
| 6,767,706 B2 | 7/2004 | Quake et al. |
| 6,814,859 B2 | 11/2004 | Koehler et al. |
| 6,885,982 B2 | 4/2005 | Harris et al. |
| 6,899,137 B2 | 5/2005 | Unger et al. |
| 6,951,632 B2 | 10/2005 | Unger et al. |
| 6,960,437 B2 | 11/2005 | Enzelberger et al. |
| 7,042,649 B2 | 5/2006 | Quake et al. |
| 7,059,348 B2 | 6/2006 | Nat |
| 7,062,418 B2 | 6/2006 | Lee et al. |
| 7,097,809 B2 | 8/2006 | Van Dam et al. |
| 7,161,736 B2 | 1/2007 | Legrand et al. |
| 7,192,629 B2 | 3/2007 | Lammertink et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,262,923 B2 | 8/2007 | Quake et al. |
| 7,279,146 B2 | 10/2007 | Nassef |
| 7,291,512 B2 | 11/2007 | Unger |
| 7,294,503 B2 | 11/2007 | Quake et al. |
| 7,368,163 B2 | 5/2008 | Huang et al. |
| 7,442,556 B2 | 10/2008 | Manger et al. |
| 7,476,363 B2 | 1/2009 | Unger et al. |
| 7,526,741 B2 | 4/2009 | Lee et al. |
| 7,604,965 B2 | 10/2009 | McBride et al. |
| 7,666,361 B2 | 2/2010 | McBride et al. |
| 7,678,547 B2 | 3/2010 | Eyal et al. |
| 7,691,333 B2 | 4/2010 | McBride et al. |
| 7,749,737 B2 | 7/2010 | McBride et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 2001/0054778 A1 | 12/2001 | Unger et al. |
| 2002/0005354 A1 | 1/2002 | Spence et al. |
| 2002/0012926 A1 | 1/2002 | Quake et al. |
| 2002/0058332 A1 | 5/2002 | Quake et al. |
| 2002/0109114 A1 | 8/2002 | Driggs et al. |
| 2002/0127736 A1 | 9/2002 | Chou et al. |
| 2002/0158022 A1 | 10/2002 | Huang et al. |
| 2002/0164816 A1 | 11/2002 | Quake |
| 2003/0008308 A1 | 1/2003 | Enzelberger et al. |
| 2003/0008411 A1 | 1/2003 | Van Dam et al. |
| 2003/0134129 A1 | 7/2003 | Lammertink et al. |
| 2003/0210997 A1 | 11/2003 | Lopez et al. |
| 2003/0217923 A1 | 11/2003 | Harrison et al. |
| 2004/0072278 A1 | 4/2004 | Chou et al. |
| 2004/0115731 A1 | 6/2004 | Hansen et al. |
| 2004/0115838 A1 | 6/2004 | Quake et al. |
| 2004/0180377 A1 | 9/2004 | Manger et al. |
| 2004/0209354 A1 | 10/2004 | Mathies et al. |
| 2004/0224380 A1 | 11/2004 | Chou et al. |
| 2004/0229349 A1 | 11/2004 | Daridon |
| 2005/0000900 A1 | 1/2005 | Huang et al. |
| 2005/0037471 A1 | 2/2005 | Liu et al. |
| 2005/0053952 A1 | 3/2005 | Hong et al. |
| 2005/0062196 A1 | 3/2005 | Hansen et al. |
| 2005/0072946 A1 | 4/2005 | Studer et al. |
| 2005/0164376 A1 | 7/2005 | Balagadde et al. |
| 2005/0221373 A1 | 10/2005 | Enzelberger et al. |
| 2006/0019267 A1 | 1/2006 | Quake |
| 2006/0172408 A1 | 8/2006 | Quake et al. |
| 2006/0196409 A1 | 9/2006 | Quake et al. |
| 2006/0233674 A1 | 10/2006 | Nelson |
| 2006/0281183 A1 | 12/2006 | Sun et al. |
| 2007/0134807 A1 | 6/2007 | Bao et al. |
| 2007/0169686 A1 | 7/2007 | Quake et al. |
| 2007/0224617 A1 | 9/2007 | Quake et al. |
| 2007/0248971 A1 | 10/2007 | Maerkl et al. |
| 2007/0254278 A1 | 11/2007 | DeSimone et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0138829 A1 | 6/2008 | Lehmann et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0168066 A1 | 7/2009 | Hansen et al. |
| 2009/0239308 A1 | 9/2009 | Dube et al. |
| 2009/0291435 A1 | 11/2009 | Unger et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |

FOREIGN PATENT DOCUMENTS

| | | |
|---|---|---|
| WO | WO 2005/030822 A2 | 4/2005 |
| WO | WO 2005/084191 A2 | 9/2005 |
| WO | WO 2007/033385 A2 | 3/2007 |
| WO | WO 2007/044091 A2 | 4/2007 |
| WO | WO 2008/043046 A2 | 4/2008 |
| WO | WO 2009/100449 A1 | 8/2009 |
| WO | WO 2010/011852 A1 | 1/2010 |
| WO | WO 2010/017210 A1 | 2/2010 |
| WO | WO 2010/077618 A1 | 7/2010 |
| WO | WO 2011/053790 A2 | 5/2011 |

OTHER PUBLICATIONS

Hong et al., "A nanoliter-scale nucleic acid processor with parallel architecture" *Nature Biotechnology*, 22(4):1-5 (2004).

Liu et al., "Solving the "world-to-chip" interface problem with a microfluidic matrix" *Analytical Chemistry* 75:4718-4723 (2003).

Quake et al., "From micro to nanofabrication with soft materials" *Science* 290:1536-1540 (2000).

Terry et al., A Gas Chromatography Air Analyzer Fabricated on a Silicon Wafer, *IEEE Trans. on Electron Devices*, v ., ED-26(12):1880-1886 (1979).

Unger et al., "Monolithic microfabricated valves and pumps by multilayer soft lithography" *Science*, 288:113-116 (2000).

Webster et al., Monolithic Capillary Gel Electrophoresis Stage with On-Chip Detector in International Conference on Micro Electromechanical Systems, *MEMS 96*, pp. 491-496 (1996).

Xia et al., "Soft lithography" *Angewandte Chemie-Inrernational Edition*, 37:551-575 (1998).

MICROFLUIDIC SIEVE VALVES

CROSS-REFERENCE TO RELATED APPLICATIONS

This application is a divisional of U.S. application Ser. No. 11/792,170, filed Jul. 15, 2008, now abandoned, which is a U.S. National Phase Application under 35 U.S.C. §371 of International Application No. PCT/US2005/043833, filed on Dec. 5, 2005, which claims benefit of U.S. Provisional Application No. 60/633,121, filed Dec. 3, 2004, the entire contents of which are incorporated herein by reference.

STATEMENT REGARDING FEDERALLY SPONSORED RESEARCH

This invention was made with government support under Grant No. CA119347 awarded by the National Institutes of Health and Grant No. DE-FC02-02ER63420 awarded by the US Department of Energy. The government has certain rights in the invention

FIELD OF THE INVENTION

The present invention relates to microfabricated devices and microchromatography.

BACKGROUND OF THE INVENTION

Microfluidic devices may be used in a variety of biomedical and pharmaceutical applications, including analysis, preparation and synthesis of chemical compounds and analysis and manipulation of cells, proteins and nucleic acids. In many applications, the ability to concentrate or chromatographically separate compounds in a microfluidic environment enhances the utility of microfluidic devices. Thus, a rapid, inexpensive and effective method for performing chromatography and for microfluidic chromatography columns would be of great benefit. The present invention meets these and many other needs.

BRIEF SUMMARY

In one aspect the invention provides a microfabricated sieve valve structure having an elastomeric membrane that separates a first channel lumen and a second channel lumen, where pressurizing the first channel over a wide range of pressures causes the membrane to be deflected into the second channel lumen and reduce the cross-sectional area of the second channel lumen by not more than 90% and not less than 50% of the cross-sectional area when the membrane is not deflected. In certain embodiments the cross-sectional profile of the second channel is rectangular. In certain embodiments pressurizing the first channel over a wide range of pressures causes the membrane to be deflected into the second channel lumen and reduce the cross-sectional area of the second channel lumen by not more than 90% and not less than 75% of the cross-sectional area when the membrane is not deflected. In certain embodiments the range of pressures is a range of at least 7 psi, optionally at least 10 psi, optionally at least 15 psi or encompasses a range of 22-26 psi, optionally 20-28 psi, and optionally 18-30 psi. In certain embodiments the sieve valve has a retention size of from 1 micron to 20 microns.

In a related aspect the invention provides a microfluidic device having two or more sieve valves. In an embodiment, a chromatographic separation medium is disposed between two sieve valves thereby forming a separation column. In an embodiment the device has more than 20 separation columns.

In a related aspect the invention provides a microfluidic device comprising a microfluidic chromatography column, the column comprising a chromatographic separation medium disposed behind a sieve valve, and optionally disposed between two sieve valves. In an embodiment the chromatographic separation medium comprises a polymeric bead coupled to a ligand. For example, in certain embodiments beads have been derivatized to bind a nucleic acid (e.g., oligo(dT)) or a protein (e.g., an antibody).

In a related aspect the invention provides a microfluidic device with two or more sieve valves paired with conventional valves. In a related aspect the invention provides a microfluidic device that contains five or more sieve valves paired with conventional valves.

In a related aspect the invention provides a method of making a microfluidic column in a microfluidic device, wherein the device comprises a flow channel and a sieve valve positioned to reduce the cross-sectional area of the lumen of the flow channel when closed. The method involves providing a suspension of chromatography beads in the flow channel ante to the sieve valve, where the valve is closed and the beads are of a size that is retained by the closed sieve valve; flowing the suspension through the flow channel, whereby the movement of the beads is impeded by the closed sieve valve and the solution in which the beads are suspended flows through the flow channel, thereby producing a column of beads in the flow channel.

In one embodiment, the device has two or more sieve valves each positioned to reduce the cross-sectional area of the lumen of the flow channel when closed, and the method of making a microfluidic column in a microfluidic device includes providing the suspension of chromatography beads ante to a second sieve valve, wherein the second sieve valve is open and is ante to the closed sieve valve, and wherein the beads are of a size that is retained by the second sieve valve; flowing the suspension of chromatographic beads through the flow channel through and past the second sieve valve, wherein the flow of the beads is impeded by the closed sieve valve and the solution in which the beads are suspended flows through the flow channel, thereby producing a column of beads in the flow channel; and, closing the second sieve valve, thereby trapping the beads betwixt the sieve valves.

In a related aspect the invention provides a method for trapping particles in a microfluidic flow channel of a microfluidic device, by providing a suspension of the particles in a flow channel ante to a closed sieve valve, wherein the particles are of a size that is retained by the closed sieve valve; flowing the suspension through the flow channel, whereby the movement of the particles is impeded by the closed sieve valve and the solution in which the particles are suspended flows through the flow channel, thereby trapping the particles in the flow channel. In one embodiment the particles are living cells.

BRIEF DESCRIPTION OF THE FIGURES

FIG. 1. Schematic representations illustrate the operation mechanisms of (A) a regular valve having a round-profiled fluidic channel and (B) a sieve valve having a rectangular-profiled fluidic channel. When pressure is introduced into the control channels, the elastic membranes expand into the fluidic channels. In a regular valve, the fluidic channel is completely sealed because of the perfect fit between the expended membranes and the round profile of the fluidic channel. In a sieve valve, the square-profiled fluidic channel is only partially closed, which allows fluid to flow through the two edges. Sieve valves can be used to confine solid objects within the fluidic channel, but allow liquid to flow through it. (C) Schematic illustration of the loading of anion exchange beads into a column module incorporating one fluidic channel and five sieve and five regular valves. [☐], open valve; [X], closed valve. A suspended solution of anion exchange beads is introduced into the column modules where five sieve valves and five regular valves operate cooperatively to trap anion exchange beads inside the fluidic channel (total volume: 10 nL). A miniaturized anion exchange column for fluoride concentration is achieved when the fluidic channel is fully loaded. (D) A snapshot of the bead-loading process in action.

FIG. 3. Microfluidic filter valve. a. Sampling of parameter space sufficient to build functional bead columns. Triangles represent the filter valve method (200×200 um valve, 13 um tall) and circles (100×100 um valve, 13 um tall) represent the previous approach using slightly opened valves (Hong et al., 2004, *Nat Biotechnol*. 22:435-9). The flow channel pressure is the pressure applied to the bead inlet and the column pressure is the pressure applied to the column valve's inlet. Parameter space is measured by if the beads escape to waste. b.-d. Optical micrographs of the filter valve. Scale bars are 100 μm. b. Top-down view of an actuated filter valve. c. Cross section of the valve and open channel above it. d. Cross section of the actuated filter valve and pinched off channel.

DETAILED DESCRIPTION

In one aspect the present invention provides a microfluidic device having at least one "sieve valve." In a related aspect the invention provides a microfluidic device having at least one chromatography module comprising a chromatographic separation medium held in place in a microfluidic channel by one or more "sieve valves," or a method for making such a module. In another related aspect, the invention provides a device adapted for forming a chromatography module as described. Other aspects of the invention will be apparent upon review of the disclosure. The sieve valves of the invention have an elastomeric component and, in a preferred embodiment, the microfluidic channel is fabricated from an elastomeric material.

Microfluidic devices, both elastomeric and nonelastomeric, are widely known. Thus, the ordinarily skilled artisan will be familiar with such devices, their components and features, and methods of fabrication. For purposes of the following discussion it is assumed the reader is familiar with microfluidic devices generally, and in particular is familiar with elastomeric devices fabricated using multilayer soft lithography (MSL) methods and comprising flow channels, control channels, valves, pumps and other microfluidic and auxiliary components. There is ample additional guidance in the scientific and patent literature (see Unger et al., 2000, *Science* 288: 113-116 and references below).

Fundamental components of the elastomeric devices of the invention are flow channels, control channels and valves, each of which will be described briefly to facilitate the discussion of aspects of the invention.

The term "flow channel" refers to a microfluidic channel through which a solution can flow. The dimensions of flow channels can vary widely but typically include at least one cross-sectional dimension (e.g., height, width, or diameter) less than 1 mm, preferably less than 0.5 mm, and often less than 0.3 mm. Different flow channels in a particular microfluidic device may have different dimensions, depending on the function of the particular channel. In some embodiments of the invention the flow channel has a low aspect ratio (e.g., a height to width ratio of less than 1:5, preferably less than 1:10; sometimes less than 1:15). For example, in one embodiment, the height of the rectangular channel in which a sieve valve is positioned is about 10 microns, with a width of 200 microns. In some embodiments of the invention, the height of the (rectangular) channel in which a sieve valve is positioned is less than about 30 microns, often less than about 20 microns, and very often less than about 15 microns.

A "control channel" is a channel separated from a flow channel by an elastomeric membrane that can be deflected into or retracted from the flow channel in response to an actuation force. The dimensions of control channels can vary widely but typically include at least one cross-sectional dimension (e.g., height, width, or diameter) less than 1 mm, preferably less than 0.5 mm, and often less than 0.3 mm. For example, in one embodiment, a control channel has dimensions of 250 micrometers wide by 250 micrometers high. In another embodiment, a control channel has dimensions of 300 micrometers wide by 50 micrometers high.

Elastomeric valves (e.g., pressure-actuated elastomeric valves) consist of a configuration in which two microchannels are separated by an elastomeric segment that can be deflected into or retracted from one of the channels (a flow channel) in response to an actuation force applied to the other channel (a control channel). In one embodiment the elastomeric segment has a substantially constant thickness (i.e., the thickness does not vary more than 25%, preferably not more than 5%). The elastomeric segment is usually between 1 micron and 50 microns in thickness, preferably between 5 microns and 20 microns in thickness. Examples of elastomeric valves include, without limitation, upwardly-deflecting valves (see, e.g., U.S. 20050072946), downwardly deflecting valves (see, e.g., U.S. Pat. No. 6,408,878), side actuated valves (see, e.g., US 20020127736). The elastomeric segment may be substantially In one embodiment the valve is a push-down valve and the elastomeric segment has a convex shaped membrane (thin in the center [e.g., 10 μm] and thicker at the edges [e.g., 46 μm]. In one embodiment the valve is a push-up valve and the elastomeric segment has a uniform thickness (e.g., 5-15 microns). In conventional valves the flow channel has a rounded surface opposite the elastomeric segment, so that the deflected membrane can form a tight seal with the inner surface of the channel. For example, in one embodiment, the flow channel section is bounded by a circular arc 300 μm in width and 50 μm in height.

Valves can be actuated by injecting gases (e.g., air, nitrogen, and argon), liquids (e.g., water, silicon oils and other oils), solutions containing salts and/or polymers (including but not limited to polyethylene glycol, glycerol and carbohydrates) and the like into the control channel, a process referred to as "pressurizing" the control channel. In addition to elastomeric valves actuated by pressure-based actuation systems, monolithic valves with an elastomeric component and electrostatic, magnetic, electrolytic and electrokinetic actuation systems may be used. See, e.g., U.S. 20020109114; U.S. 20020127736, and U.S. Pat. No. 6,767,706.

Sieve Valves

A sieve valve (also called a "filter valve") is a type of elastomeric valve. Like a conventional valve, the sieve valve consists of a configuration in which a control channel and a flow channel are separated by an elastomeric segment that can be deflected into the flow channel in response to an actuation force applied to the control channel. However, in the sieve valve, small gap(s) between the elastomeric segment and the flow channel walls permit fluid to flow through the channel even with the elastomeric segment is maximally deflected into the flow channel.

Sieve valves are represented schematically in FIG. 1. The figure illustrates the operation mechanisms of (A) a regular valve having a round-profiled fluidic channel and (B) a sieve valve having a rectangular-profiled fluidic channel. When pressure is introduced into the control channel to actuate the regular valve or sieve valve, the elastic membranes deflect into the fluidic channels. In general, when valves operate, the valve membranes deflect in an elliptic shape. In the case of normal valve (FIG. 1A), the deflected membrane is fully compliant to the round-profile fluidic channel lead to complete close of the valve. For a sieve valve (FIG. 1B), a deflected membrane partially closes the valve, for example generating two small gaps the two channel edges of a rectangular-profile channel through which fluid can flow.

This property of sieve valves renders them useful in making on-chip microchromatographic columns. Since the sieve valves can be used to confine solid objects within the fluidic channel, but allow liquid to flow through it, when a suspension of a particulate chromatographic separation material ("beads" or "chromatography beads") is introduced into the flow channel the beads are trapped by the closed sieve valve and while the solution is allowed to pass through. By using this design, a variety of miniaturized columns filled with different type of beads (e.g., ion exchange resin, affinity resin, size exclusion, etc.) can be produced for applications such as ion extraction, filtration, purification, concentration and separation, and chromatography. In some embodiments the chromatography beads are roughly spherical and have diameters of between about 1 micron and 15 microns, such as approximately 1, approximately 2, approximately 3, approximately 4, approximately 5, approximately 6, approximately 7, approximately 8, approximately 9, approximately 10, approximately 11, approximately 12, approximately 13, or approximately 14 microns.

In a preferred embodiment, the elastomeric segment of the sieve valve is upwardly deflecting, as shown in FIG. 1. However, downward and sideways deflecting channels, for example, can also be used.

In a sieve valve is comprised of an elastomeric segment that can be deflected into a channel true "rectangular-profiled" fluidic channel. In general, in a cross-sectional profile of the portion of the channel opposite the elastomeric segment does not have the shape of a section (arc) of a circle or ellipse or other conical section (assuming an orientation in which the elastomeric segment is located at the concave face of the circle or ellipse). In one common embodiment, as illustrated in FIG. 1B, a sieve valve is comprised of an elastomeric segment that can be deflected into a true "rectangular-profiled" fluidic channel. "Rectangular-profiled" means the cross-section has the profile of a rectangle, and comprises first and second sides, which are opposite each other and of approximately equal length, and a third side (floor) at right angles to the first and second sides. It will be appreciated that deflection of the elastomeric segment onto channels with somewhat different profiles will also achieve the desired result of allowing liquid to flow through will retaining particles. Thus, in alternative embodiments the cross-sectional profile of the channel is not truly rectangular but has a different shape that precludes the elastomeric segment from entirely blocking the channel into which it is deflected. For example, in one embodiment, the cross-section has the profile of one-half of a rounded rectangle. A rounded rectangle is the shape obtained by taking the convex hull of four equal circles of radius (r) and placing their centers at the four corners of a rectangle with side lengths a and b. The rounded rectangle has area (A) and perimeter (p) as follows: $A=ab+2r(a+b)+\pi r^2$ and $p=2(a+b+\pi r)$. In a preferred embodiment the profile of the flow channel is rectangular. In one embodiment, sieve valves are present on a portion of the flow channel that is 200 microns wide, 13 microns high, and has a rectangular profile.

Figure 1A:
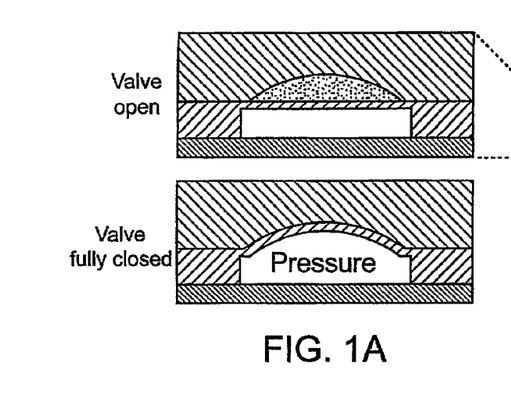
Figure 1B:
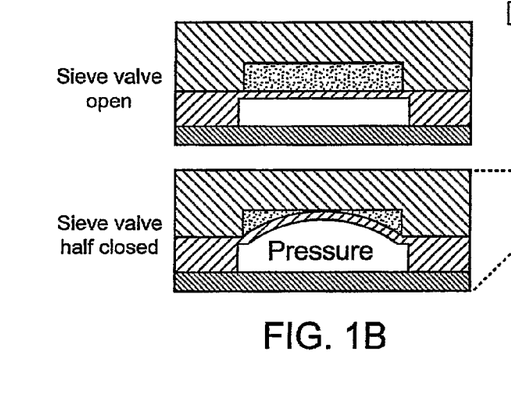

As illustrated in FIG. 1A, when the sieve valve is closed, the deflected elastomeric membrane contacts a wall of the flow channel that lies opposite the membrane. This generates two small gaps the two channel edges of a rectangular-profile channel, through which fluid can flow ("flow gaps"). Both of the gaps are considered in determining the cross-sectional area of the lumen when the valve is closed. A particular advantage of the present invention is the ability of sieve valves to function over a wide range of actuation pressures. This represents a significant advance over previous designs in which a "slightly opened" valve present on a flow channel with a semicircular profile allowed fluid, but not particles, to pass through (see Hong et al., 2004, *Nat Biotechnol.* 22:435-9; see U.S. 2005/0053952). The flow gap generated by the "slightly opened" valves varies continuously with changes in actuation pressure (i.e., an "analog" filter valve that may be more open or less open) while the sieve valve creates flow gaps of more-or-less constant size over a broad range of actuation pressures (i.e., an "digital valve" that is open or closed, with gaps).

A sampling of parameter space sufficient to build functional bead columns by the two methods is shown in FIG. 3. The experiment either applied 1.5 psi pneumatic pressure to the bead inlet while varying the valve's pressure, or kept the column valve's pressure constant while varying the pressure applied to the flow inlet. Using the sieve valves, flow pressure can be varied by an order of magnitude more than the "slightly opened" valves, measured by whether or not beads escape to waste (FIG. 3). Similarly, when applying constant pressure to the bead inlet, the pressure applied to the sieve valve used to stack the beads can be varied seven-fold more than the "slightly opened" valves.

The proportion of the cross-sectional area of the channel that remains open when the sieve valve is closed is another characteristic feature of the valve, and can be adjusted by varying the height and width of the flow chamber profile, the pressure applied to the sieve valve, the length, width, and thickness of the membrane, the flexibility of the membrane (Young's modulus), and the applied actuation force. See US Pat. App. 2005/0053952 for a discussion. When the membrane is fully deflected into the flow channel lumen the cross-sectional area of the lumen is reduced but is not fully blocked. Usually the cross-sectional area of the lumen is reduced by at least 30%, more often at least 40% and preferably by at least 50%. Preferably, when the membrane is fully deflected into the flow channel lumen the cross-sectional area of the lumen is reduced to from 5% to 50% (more often 10% to 50%, and very often from 10% to 25%) of the cross-sectional area of the lumen when the membrane is not deflected. That is, in some embodiments fully actuating the sieve valve results in a reduction in the lumen size by 50% to 90%, preferably from 75 to 90%. In the case in which two small gaps are maintained at the two channel edges of a rectangular-profile channel, both of the gaps are considered in determining the cross-sectional area of the lumen when the valve is closed.

As noted above, in general, a sieve valve of the present invention will remain closed with gaps over a wide range of actuation pressures and flow channel pressures. Thus, the present invention provides a valve that remains deflected into the flow channel lumen sufficient to reducing the cross-sectional area of the lumen by from 50% to 90%, preferably by from 75 to 90% over a wide range of flow pressures and/or actuation pressures. In this context, "a wide range" means a range of at least 7 psi (e.g., from 16-23 psi, or 18 to 25 psi) and preferably a range of at least 10 psi (e.g., from 16-26 psi, or 20 to 30 psi), and most preferably a range of at least 14 psi (e.g., from 16-30 psi, or 18 to 32 psi). In other particular embodiments, the wide range is at least 7, at least 8, at least 9, at least 11, least 12, at least 13, at least 15, or at least 16 psi. In particular embodiments, the range of pressures encompasses a range of 22-26 psi, alternatively 20-28 psi, alternatively 18-30 psi, alternatively 16-20 psi. In certain embodiments the sieve valve having these properties has a width of from 50 to 300 microns, a length of from 50 to 300 microns, and is deflected into a channel depth of 5 to 30 microns. Preferably the sieve valve membrane has a width of from 100 to 300 microns, a length of from 100 to 300 microns, and is deflected into a channel with a depth of 10 to 20 microns. Preferably the sieve valve has a width of from 100 to 200 microns, a length of from 100 to 200 microns, and is deflected into a channel with a of 10 to 20 microns. In one embodiment the sieve valve membrane is approximately square and has width and length dimensions of 100 to 300 microns (e.g., 100×100, 150×150, 200×200, and 250×250 microns) and has a channel depth of 5 to 30 microns, preferably 10 to 20 microns.

It will be apparent that in normal operation, the flow channel lumen is not completely blocked by the membrane when the sieve valve is fully actuated, e.g., when the control channel is maximally pressurized. "Maximally pressurized" refers to the maximum pressure applied to the control channel in the normal functioning of the valve, or alternatively refers to the pressure above which the device will fail (e.g., delaminate).

In particular embodiments valves (including valves with dimensions as described above) do not completely block the flow channel lumen with the membrane is fully actuated by a control channel pressure of 30, 32, 34, 35, 38 or 40 psi.

"Retention size" is another characteristic feature of a sieve valve. "Retention size" refers to the diameter of a spherical particle, i.e., bead, that is retained by the sieve valve when actuated. Accordingly, in preferred embodiments the retention size of a sieve valve is about 1 micron, about 2 microns, about 3 microns, about 4 microns, about 5 microns, about 6 microns, about 7 microns, about 8 microns, about 9 microns, about 10 microns, about 11 microns, about 12 microns, about 13 microns, about 14 microns, about 15 microns, or larger than about 15 microns. (It will be apparent that a sieve valve with a retention size of 1 micron will also trap larger beads.) In general, the optimal diameters of beads for use in chromatography are in the range of 2 µm to as 50 µm, depending on the specific geometry to the channels and valves. Retention size can be calculated or measured. One way to measure retention size is to use a roughly spherical polymeric bead of known diameter (e.g., 3 microns) and determining whether or not the bead is retained by the valve. Beads that may be used include polystyrene beads. In one embodiment, the beads are monosized polymer particles known as DYNABEADS (Invitrogen Corp. Carlsbad, Calif.).

Microfluidic Column Module

A microfluidic column module of the invention has one or more sieve valves, and a chromatographic separation medium disposed adjacent to a sieve valve or between a pair of sieve valves. For clarity, the terms "ante" or "ante-valve," "post" or "post-valve," and "betwixt" can be used to describe a position in a flow channel relative to a sieve-valve and the direction of fluid flow in the channel. "Ante" refers to a position upstream of valve. For example, to produce a chromatography column, chromatographic separation material is introduced ante (see FIG. 1C). "Post" refers to a position downstream of valve. "Betwixt" refers to the region of a microfluidic flow channel between two sieve valves (e.g., the separation material-containing region of the flow channel in FIG. 1).

As described above, a microfluidic chromatography column can be prepared by introducing a suspension (e.g., an aqueous suspension) of a particulate chromatographic separation material ("beads") ante to a closed sieve valve, allowing the beads to be trapped. In a preferred embodiment a second sieve valve ante to the first is then closed to confine the separation material. Thus, the chromatography beads lie between the two valves. The second sieve valve is useful to contain the beads and permits fluid to be flowed through the column in either direction. It will be immediately recognized that the ability to flow solution in both directions through a column has a number of applications, including applications in chromatography.

A variety of different chromatography beads may used in the column module. For example and without limitation, chromatographic separation material can include a bead material (e.g., cross-lined agarose or dextran beads, functionalized silica, polymer-coated silica, or porous silica particles, resins such as copolymers of styrene and divinylbenzen, and divinylbenzene and acrylic or methacrylic acid, metal and other materials) which may be derivatized, bound to or coated with a compound(s) that specifically interacts with a compound in solution as it passes through the column. For example and without limitation, chromatographic separation material can be adapted for many types of chromatography including gel filtration, anion exchange, cation exchange, hydrophobic interaction, size exclusion, reverse phase, metal ion affinity chromatography, IMAC, immunoaffinity chromatography, and adsorption chromatography. For example and not limitation chromatographic separation material that can be used in the column module can be HEI X8 (BioRad Corp.).

Figure 1C:
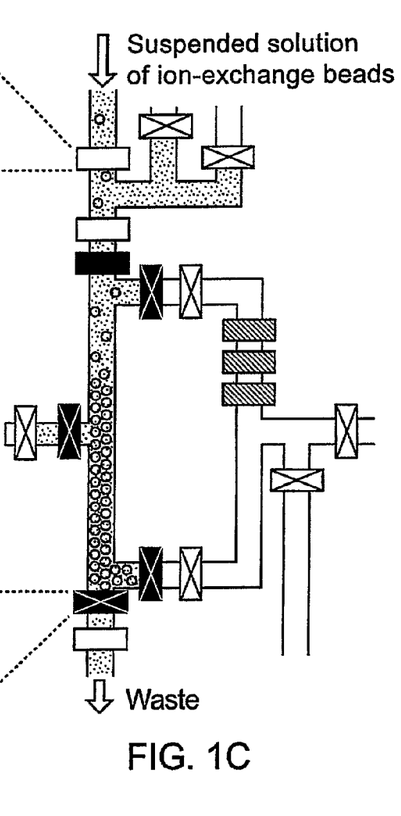
Figure 1D:
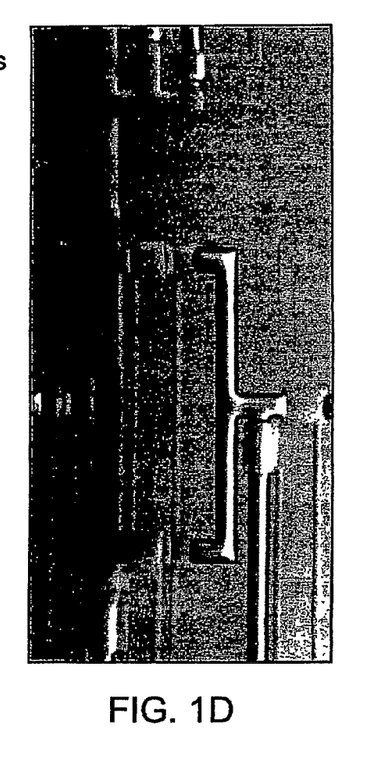
Figure 2:
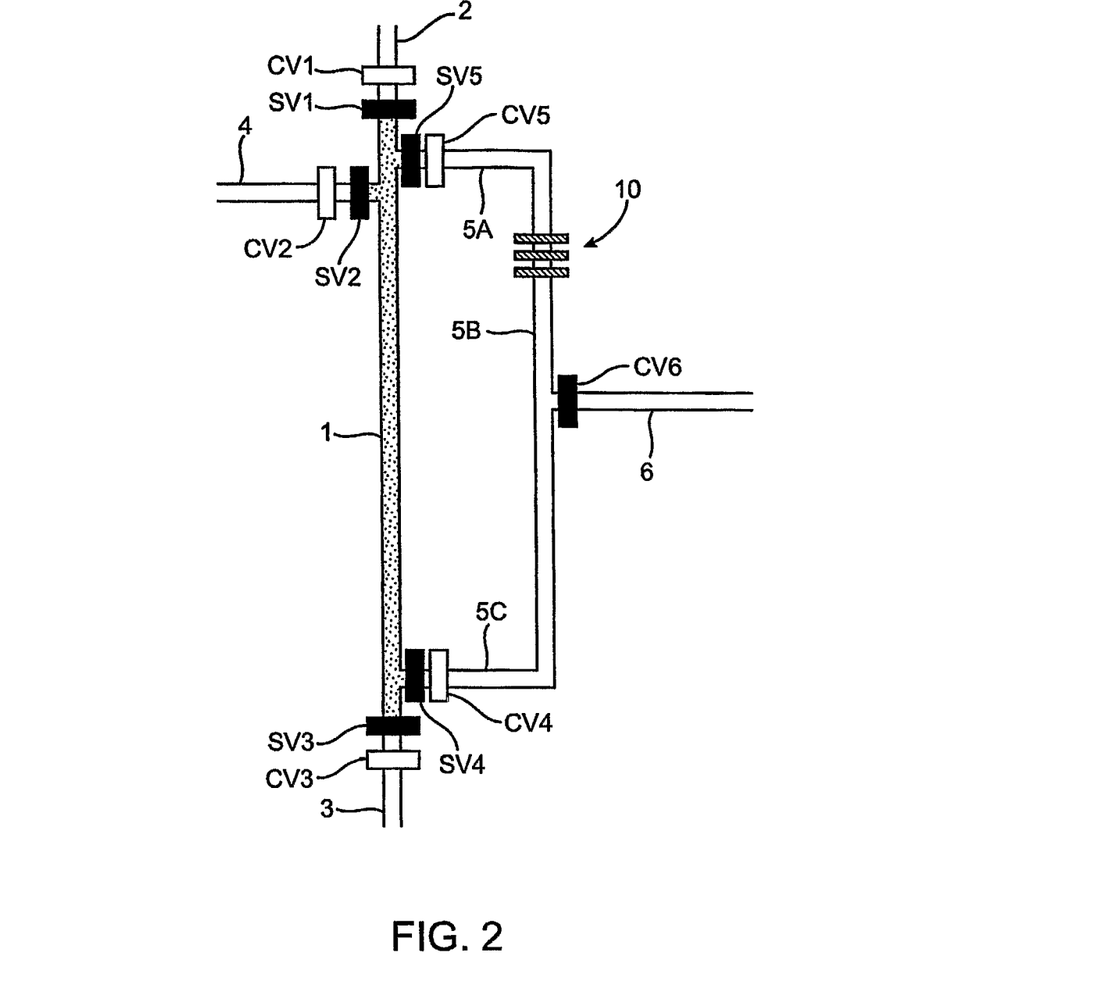
FIG. 2. A schematic representation corresponding to the column module of FIG. 1.
Figure 3A:
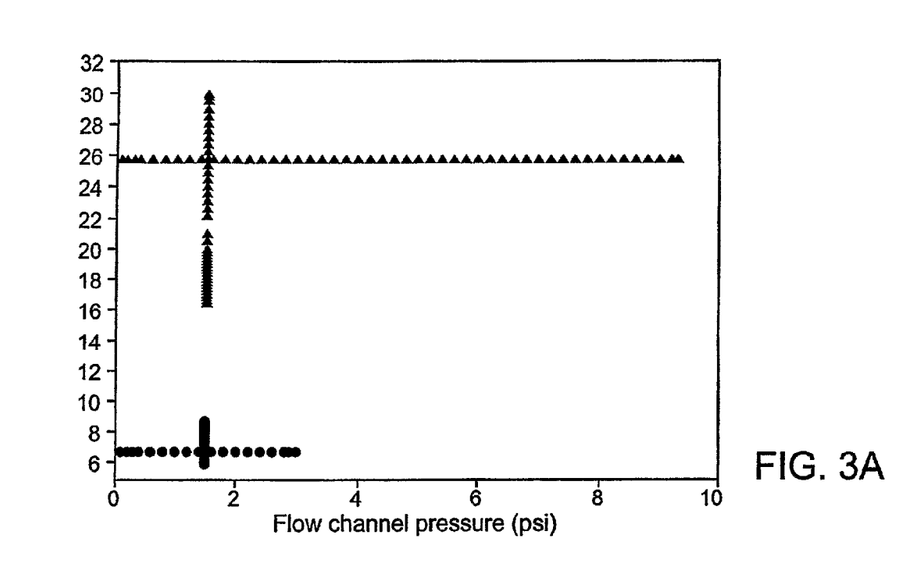
Figure 3B:
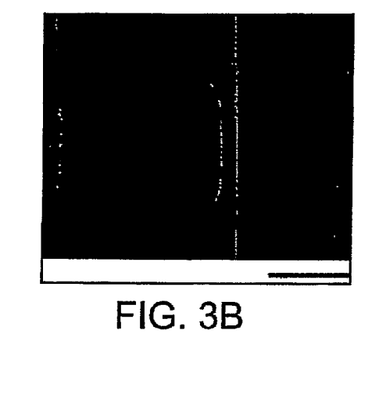
Figure 3C:
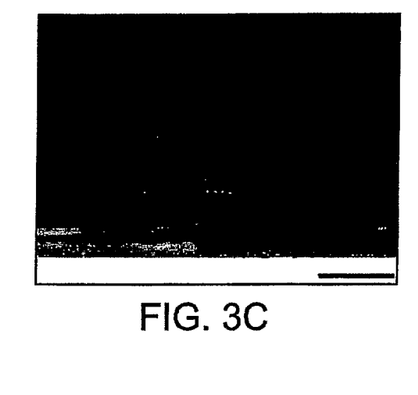
Figure 3D:
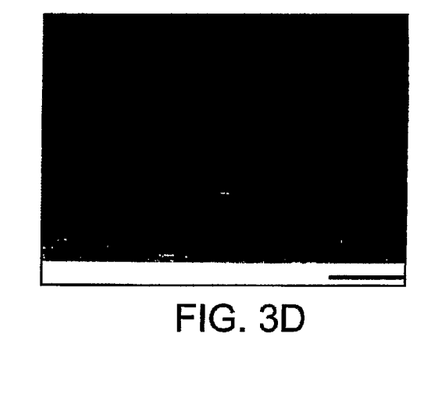

In some embodiments, the region of the flow channel in which the chromatographic material is disposed (betwixt two sieve valves) is in fluidic communication with one, two, three or more than three branch flow channels for which there are additional sieve valves and/or conventional valves situated near the junction of the main flow channel and branch flow channels, as shown in FIGS. 1 and 2. This arrangement facilitates the use of the column for separations, concentrations and the like.

In certain embodiments, a number of sieve valves are used. As illustrated in the Figures, sieve valves and conventional valves can work in concert in the construction and use of a microfluidic column. FIG. 1C is a schematic illustration of the loading of anion exchange beads into a column module incorporating one fluidic channel and five sieve and five regular valves. [☐], open valve; [X], closed valve. A suspended solution of anion exchange beads is introduced into the column modules where five sieve valves and five regular valves operate cooperatively to trap anion exchange beads inside the fluidic channel (total volume: 10 nL). A miniaturized anion exchange column for fluoride concentration is achieved when the fluidic channel is fully loaded (See FIG. 1D).

With reference to FIG. 2, for example, to generate a microfluidic column in flow channel 1, a suspension of chromatographic beads introduced through flow channel 2 (column inlet) through open conventional valve CV1 and open sieve valve SV1. The suspension solution flows through closed sieve valve SV2 and open conventional valve CV2 to flow channel 3 (column outlet) while the beads are retained by closed sieve valves SV2-5. Conventional valves CV2, and CV4-6 are also closed. Flow channels 1-3 are segment of the same channel in this example. After loading the beads, sieve channel SV1 can be closed to retain the beads. A sample mixture may be flowed through the column, in either direction, with all valves except CV1 and CV3 closed. Additional reagents, eluants or the like may be introduced thorough flow channel 4 through open valve CV2 and closed valve SV2 with valves SV1-5, valves CV4 and CV5 closed and either or both of CV1 and CV3 open.

Sieve valves may be used in a column module to circulate a solution thought the column (either to increase the efficiency of loading of a sample or of elution into a small volume). With reference to FIG. 2, by the action of peristaltic pump 10 a solution can be circulated through closed path formed by flow channels 1 and 5A-C when valves CV1-3, CV6 and SV1-5 closed, and CV4 and 5 are open. The solution can then be removed through any of flow channels 2-4 or 5D. Optionally the solution can be displaced by introducing another solution through a different flow channel.

As illustrated in the figures and discussion above, sieve valves are often paired with a conventional valve to separately control flow of particles and liquid. In one embodiment the invention provides a device having at least one sieve valve paired with a conventional valve. As used in this context, valves are paired when they are proximal to each other. For example, in some embodiments, no more than 200 microns (alternatively, not more than 150 microns, or 100 microns) separates the region of a flow channel blocked by the conventional valve (when actuated) and the region blocked by the sieve valve (when actuated), measured valve edge to valve edge. In one embodiment many (i.e., at least 20%) or most (i.e. at least 50%) functioning sieve valves in a device are paired with a conventional valve.

In one aspect the invention provides a method of making a microfluidic column in a microfluidic device by providing a suspension of chromatography beads in the flow channel ante to a closed sieve valve (where beads are of a size that is retained by the closed sieve valve); flowing the suspension through the flow channel so that the movement of the beads is impeded by the closed sieve valve and the solution in which the beads are suspended flows through the flow channel, thereby producing a column of beads in the flow channel. In this context "providing a suspension" means introducing the suspension ante to the sieve valve by flowing the suspension in a flow channel in the microfluidic device. The suspension may be introduced from an external reservoir , or from another part of the device, for example. After the beads are trapped, a second sieve valve can be closed to trap the beads (or other particles) between two sieve valves.

Microfluidic Device

A device of the invention may have multiple chromatography modules which may be function in the purification, concentration, or separation of a variety of compounds including biomolecules (e.g., nucleic acids, proteins, sugars), products and reactants of chemical reactions, and the like.

Usually a device will have a combination of sieve valves and conventional (fully closable) valves. In one embodiment the ratio of conventional valves to sieve valves will be greater than or equal to 2:1, 3:1, 4:1, 5:1, 6:1, 10:1 or higher. In one embodiment the device has flow channels with a rectangular profile throughout the length of the channel and also has non-rectangular flow channels . In one embodiment the device has flow channels that have a rectangular profile in certain regions of the channel and a non-rectangular profile in other regions.

Figure 4:
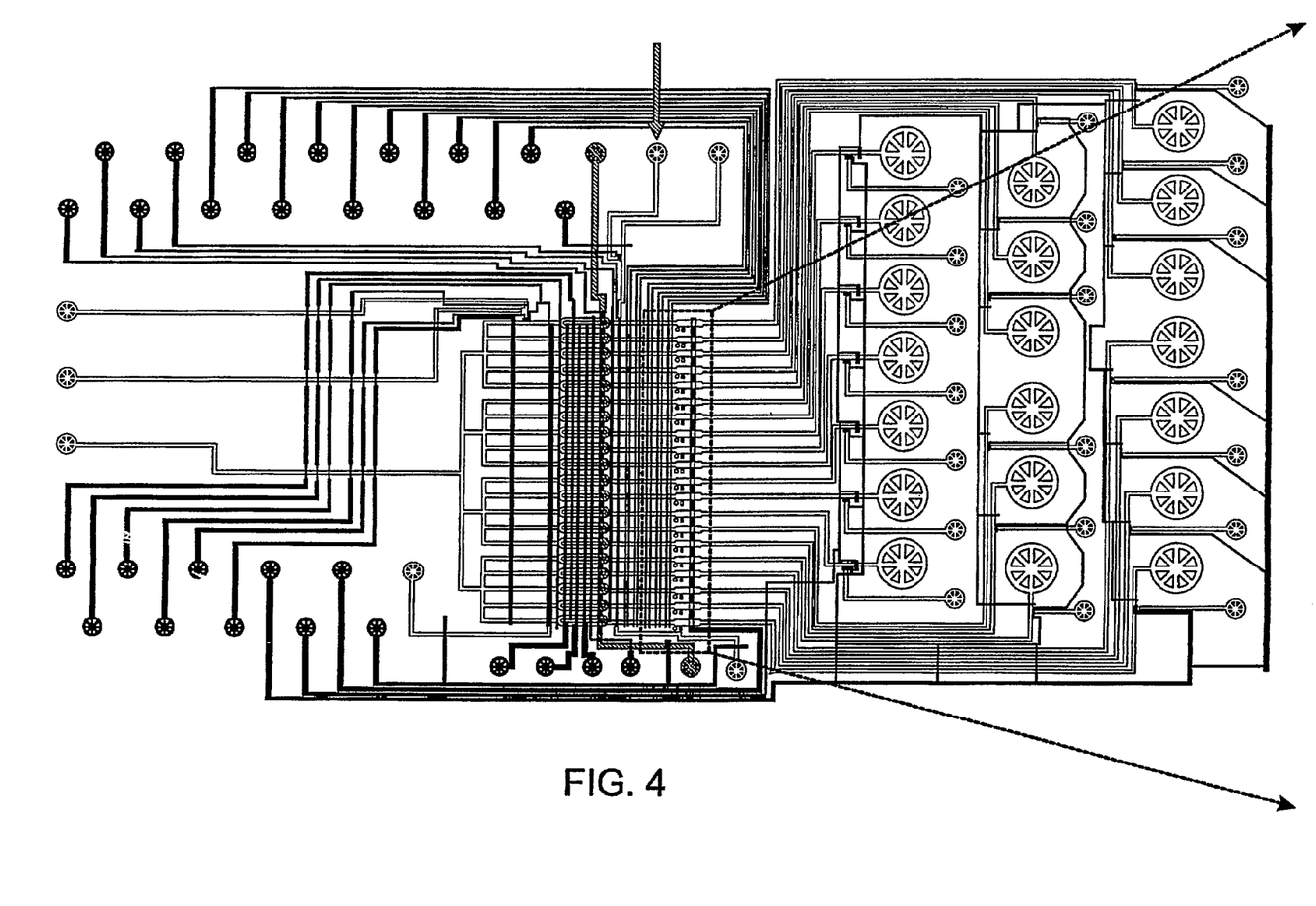
FIG. 4. A microfluidic device with 20 columns (yellow) in multiplex format. Flow channels are shown in white and control channels in purple. Scale bars are 800 μm.

A device of the invention may have one column or more than one column (e.g., 1-5 columns, 5-10 columns, 10 to 1000 columns or more than 1000 columns). FIG. 4 shows schematic of a device with 20 columns arranged in parallel. The microfluidic device can be used to conduct separations in a multiplexing format, thus allowing multiple analyses to be conducted simultaneously. In the device illustrated in FIG. 4, beads (e.g., paramagnetic beads derivatized with oligo(dT)$_{25}$ sequence (Dynal Biotech) can be distributed serially (1 to 4 at a time) into 20 columns (rectangular box) and held in place with sieve valves. Reagent(s) can be directed over each of the columns and a target molecule (e.g., RNA from an individual cell) can be captured by the affinity beads. Waste (loading solution, wash buffers, etc.) can flow through the column to waste ports (small wagon wheels) for removal. Once the target molecules have bound to beads in each column, the sieve valves can be opened and the beads allowed to flow to ports (large wagon wheels) for collection. Alternatively, the target molecules can be eluted from the beads and collected. In still another approach, the target molecules can be manipulated on column. For example, bound RNA can be reverse transcribed on column by, for example, flushing the columns with reverse transcriptase and dNTPs in a first strand reaction buffer for 45 minutes, and bringing the chips to 40 degrees C. in a thermal microscope stage to activate the polymerase. Oligo(dT) sequences on the beads act as primers. When cDNA synthesis is complete, the bead:cDNA complexes are sent to the output ports in PCR buffer and collected for analysis.

Uses of Sieve Valves

The sieve valves of the invention and microfluidic devices containing have a wide variety of uses. In particular, the uses of sieve valves are not limited to conventional chromatography modules.

In one aspect, a sieve valve can be used to collect any sort of particle and hold them in place. In one embodiment, the particle is a chromatography separation medium such as, for example, a polymeric bead coupled to a ligand. Such beads can be used to capture the corresponding anti-ligand in a sample. In some embodiments, the beads are derivatized to bind a nucleic acid (e.g., coupled to a complementary RNA, DNA, PNA, or the like). In some embodiments, the beads are coupled to an antibody, an antigen, a protein, protein A, biotin, steptavidin, a receptor, a probe, or any other molecule with an affinity for the desired target. Useful polymeric beads are available from commercial suppliers. For example, DYNABEADS (Invitrogen Corp., Carlsbad, Calif.) may be used.

For example, beads coated with an anti-ligand (e.g., antibody) can be circulated through flow channels of a device and captured in a sieve valve; a solution carrying the ligand can be flowed through the captured beads and the ligand bound to the surface via the anti-ligand. The trapped particles may be processed in place without opening the valves and/or they may be released by opening the sieve valve(s). For example, at a desired time the sieve valve may be opened and the beads allowed to flow to other locations on or off the chip, thereby delivering the ligand to the new locations.

In another example, cells may be captured by a sieve valve. In one example, a lysis solution flowed through the collected cells and cell components (e.g., small soluble molecules) may then flow through the sieve valve while unlysed cells or debris are retained. In another example, cells may be captured by a sieve valve and then a chemical or immunological stain is flowed through the collected cells, staining all or some of the captured cells. The sieve valves can then be released and the cells transported to other locations. In another example, a solution containing cells or other particles may be flowed through a sieve valve and the cells or particles retained, thus concentrating the cells or particles. A more concentrated solution of cells or particles may be captured by opening the sieve valve or reversing the direction of flow (so that solution flows through the sieve valve towards the cells or particles. Numerous other applications will be apparent upon review of the disclosure.

Elastomeric Fabrication

As noted above, microfluidic devices, both elastomeric and nonelastomeric, are well known, and the ordinarily skilled artisan will be familiar with such devices, their components and features, and methods of fabrication. In preferred embodiments, the device is fabricated using elastomeric materials. Methods of fabrication using elastomeric materials, and devices made using such materials, have been described in detail (see, e.g., Unger et al., 2000, *Science* 288: 113-116; US 2004/0115838; and PCT publications WO 01/01025; WO 2005/030822 and WO 2005/084191) and will only be briefly described here.

Sieve valves can be constructed using standard optical lithography processes followed by multilayer soft lithography (MSL) methods (Unger et al., Science 2000, 288: 113-16). For example, a device with sieve valves, designed for the purpose of capturing mRNA from single cells, has been constructed of three layers of the silicone elastomer polydimethylsiloxane (PDMS) (General Electric) bonded to a RCA cleaned #1.5 glass coverslip. The device was fabricated as described in Fu et al., *Nat Biotechnol* 1999, 17: 1109-11 with slight modifications (Studer et al., *J. Appl. Phys.* 2004, 95: 393-98). Negative master molds were fabricated out of photoresist by standard optical lithography and patterned with 20,000 dpi transparency masks (CAD/Art Services) drafted with AutoCAD software (Autodesk). The flow layer masks (column portion and channel portion) were sized to 101.5% of the control layer masks to compensate for shrinking of features during the first elastomer curing step. The flow master molds were fabricated out of 40 µm AZ-100XT/13 µm SU8-2015 photoresists (Clariant/Microchem) and the control molds were cast from 24 µm SU8-2025 (Microchem).

In order to implement sieve valves, the flow channel portion where columns are to be constructed has a rectangular profile in cross section. Therefore, in one embodiment, a multistep lithography process is used for microfluidic devices composed of both sieve valves and conventional valves (Unger et al., 2000, *Science* 288: 113-116). In one approach, for example, the column resist is spun onto a silicon wafer and processed, followed by processing the resist for the conventional fluid channels. The fabrication of molds having a rounded flow structure is achieved by thermal re-flow of the patterned photoresist. Negative photo-resists such as SU8 rely on thermal polymerization of UV-exposed regions, and therefore can not be reflowed. In order to be compatible with membrane valves, flow channel sections are defined using a positive photoresist such as AZ-50 (Clariant Corp. Charlotte, N.C.).

Once the fluid channels are processed, the two layer mold is heated (e.g., baked on a hot plate of 200 degrees C. for 2 hours) so that the photoresist can reflow and form a rounded shape, which is important for complete valve closure (see Unger, supra). A hard bake step is also implemented between resist steps, in order to make the column resist mechanically robust for downstream processing. Most devices that have sieve valves also have conventional valves, and have both rounded and non-rounded (e.g., rectangular) flow channels.

A large variety of elastomeric materials may be used in fabrication of the devices of the invention. Elastomers in general are polymers existing at a temperature between their glass transition temperature and liquefaction temperature. See Allcock et al., *Contemporary Polymer Chemistry*, 2nd Ed.

For illustration, a brief description of the most common classes of elastomers is presented here:

Silicones: Silicone polymers have great structural variety, and a large number of commercially available formulations. In an exemplary aspect of the present invention, the present systems are fabricated from an elastomeric polymer such as GE RTV 615 (formulation), a vinyl-silane crosslinked (type) silicone elastomer (family). The vinyl-to-(Si—H) crosslinking of RTV 615 allows both heterogeneous multilayer soft lithography and photoresist encapsulation. However, this is only one of several crosslinking methods used in silicone polymer chemistry and suitable for use in the present invention. In one embodiment, the silicone polymer is polydimethylsiloxane (PDMS).

Perfluoropolyethers: Functionalized photocurable perfluoropolyether (PFPE) is particularly useful as a material for fabricating solvent-resistant microfluidic devices for use with certain organic solvents. These PFPEs have material properties and fabrication capabilities similar to PDMS but with compatibility with a broader range of solvents. See, e.g., PCT Patent Publications WO 2005030822 and WO 2005084191 and Rolland et al., 2004, "Solvent-resistant photocurable "liquid Teflon" for microfluidic device fabrication" *J. Amer. Chem. Soc.* 126: 2322-2323.

Other suitable materials include polyisoprenes, polybutadienes, polychloroprenes, polyisobutylenes, poly(styrene-butadiene-styrene)s, polyurethanes, poly(bis(fluoroalkoxy) phosphazene) (PNF, Eypel-F), poly(carborane-siloxanes) (Dexsil), poly(acrylonitrile-butadiene) (nitrile rubber), poly (1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

In an alternative embodiment, microfluidic devices can be fabricated in a variety of nonelastomeric materials including silicon, glass, metal, ceramic and nonelastomeric polymers in which an elastomeric segment is deflected into a nonelastomeric channel. Composite structures are described in, for example, US 20020127736.

Additional guidance can be found in the scientific and patent literature including, but not limited to the following: Unger et al., 2000, *Science* 288: 113-116; Quake & Scherer, 2000, "From micro to nanofabrication with soft materials" *Science* 290: 1536-40; Xia et al., 1998, "Soft lithography" *Angewandte Chemie-International Edition* 37: 551-575; Unger et al., 2000, "Monolithic microfabricated valves and pumps by multilayer soft lithography" *Science* 288: 113-116; Thorsen et al., 2002, "Microfluidic large-scale integration" *Science* 298: 580-584; Chou et al., 2000, "Microfabricated Rotary Pump" *Biomedical Microdevices* 3: 323-330; Liu et al., 2003, "Solving the "world-to-chip" interface problem with a microfluidic matrix" *Analytical Chemistry* 75, 4718-23," Hong et al, 2004, "A nanoliter-scale nucleic acid processor with parallel architecture" *Nature Biotechnology* 22: 435-39; Fiorini and Chiu, 2005, "Disposable microfluidic devices: fabrication, function, and application" *Biotechniques* 38: 429-46; Beebe et al., 2000, "Microfluidic tectonics: a comprehensive construction platform for microfluidic systems." *Proc. Natl. Acad. Sci. USA* 97: 13488-13493; Rolland et al., 2004, "Solvent-resistant photocurable "liquid Teflon" for microfluidic device fabrication" *J. Amer. Chem. Soc.* 126: 2322-2323; Rossier et al., 2002, "Plasma etched polymer microelectrochemical systems" *Lab Chip* 2: 145-150; Becker et al., 2002, "Polymer microfluidic devices" Talanta 56:267-

287; Becker et al., 2000, "Polymer microfabrication methods for microfluidic analytical applications" *Electrophoresis* 21: 12-26; Terry et al., 1979, A Gas Chromatography Air Analyzer Fabricated on a Silicon Wafer, *IEEE Trans. on Electron Devices*, v. ED-26, pp. 1880-1886; Berg et al., 1994, *Micro Total Analysis Systems*, New York, Kluwer; Webster et al., 1996, *Monolithic Capillary Gel Electrophoresis Stage with On-Chip Detector* in International Conference On Micro Electromechanical Systems, *MEMS* 96, pp. 491496; and Mastrangelo et al., 1989, *Vacuum-Sealed Silicon Micromachined Incandescent Light Source*, in Intl. Electron Devices Meeting, *IDEM* 89, pp. 503-506; U.S. Pat. No. 6,960,437 (Nucleic acid amplification utilizing microfluidic devices); U.S. Pat. No. 6,899,137 (Microfabricated elastomeric valve and pump systems); U.S. Pat No. 6,767,706 B2 (Integrated active flux microfluidic devices and methods); U.S. Pat No. 6,752,922 (Microfluidic chromatography); U.S. Pat. No. 6,408,878 (Microfabricated elastomeric valve and pump systems); U.S. Patent Application publication Nos. 20050072946; 20050000900; 20020127736; 20020109114; 20040115838; 20030138829; 20020164816; 20020127736; 20040229349; 20040224380; 20040072278 and 20020109114; and PCT patent publications WO 2005/084191; WO05030822A2; and WO 01/01025.

EXAMPLE

Protocols For Making Device With Microfluidic Sieve Valve

Making Su8-2010 10 μm/Spr220-7 15 μm/AZ-50 40 μm flow molds &*&
1. Spin Su8-2025 at 3000 rpm for 45 s. with an acceleration of 10.
2. Soft bake mold for 1 min./3 min. at 65° C./95° C.
3. Expose mold 50 s. real time on MJB mask aligner (7 mW/cm2).
4. Bake mold post-exposure for 1 min./3 min. at 65° C./95° C.
5. Develop in Su8 nano developer. Rinse in fresh Su8 nano developer and determine if developed by looking at mold under microscope.
6. Once developed, hard bake mold at 150° C. for 2 hr.
7. Expose mold to HMDS vapor for 90 s.
8. Spin Spr220-7 (cold, straight from refrigerator) at 1500 rpm for 1 min. with an acceleration of 15.
9. Soft bake mold for 90 s. at 105° C.
10. Expose mold under a 20,000 dpi positive transparency mask (CAD/Art Services) for 3.2 min. real time on MJB mask aligner (POWER).
11. Develop mold in MF-319 developer and rinse under a stream of $H_2O$. Determine if developed by looking at mold under microscope. Spr develops rather quickly, except for areas around the Su8 layer. Therefore, some areas may get overdeveloped when trying to remove residual resist around Su8 portions.
12. Hard bake 2 hr. at 200° C.
13. Expose mold to HMDS vapor for 90 s.
14. Spin AZ-50 (cold, straight from refrigerator) at 1600 rpm for 1 min. with an acceleration of 15.
15. Soft bake mold for 1 min./5 min./1 min. at 65° C./115° C./65° C.
16. Expose mold under a 20,000 dpi positive transparency mask (CAD/Art Services) for 4 min. real time on MJB mask aligner (7 mW/cm2).
17. Develop mold in 3:1 $H_2O$:2401 developer. Rinse mold under a stream of $H_2O$.
18. Once developed (determine by visualization under microscope), reflow/hard bake 3 hr. at 200° C. Note: Temperatures for hard bakes are ramped up and down from room temperature by either turning on or off the hot plate. This will prevent resist cracking.

Making Su8-2025 23 μm Control Molds
1. Spin Su8-2025@3000 rpm for 45 s. with an acceleration of 10.
2. Soft bake mold for 2 min./5 min. at 65° C./95° C.
3. Expose mold under a 20,000 dpi negative transparency mask (CAD/Art Services) 1.2 min. real time on MJB mask aligner (7 mW/cm2).
4. Bake mold post-exposure for 2 min./5 min. at 65° C./95° C.
5. Develop in Su8 nano developer. Rinse in fresh Su8 nano developer and determine if developed by looking at mold under microscope.
6. Once developed, bake mold at 95° C. for 45 s to evaporate excess solvent.

Fabrication of 3-Layer RTV Device With Push-Up Valves
1. Prepare 5:1 GE RTV A:RTV B (mix 1 min., de-foam 5 min.).
2. Expose flow mold to TMCS vapor for 2 min.
3. Pour 30 g 5:1 GE RTV A:RTV B on respective flow mold.
4. De-gas flow mold under vacuum.
5. Bake flow mold 45 min. at 80° C.
6. While flow mold is de-gassing, prepare 20:1 GE RTV A:RTV B (mix 1 min., de-foam 5 min.).
7. Expose control mold to TMCS vapor for 2 min.
8. Spin 20:1 RTV mix at 2000 rpm for 60 s. with a 15 s. ramp.
9. Let RTV settle on control mold for ~30 min. before baking 30 min. at 80
10. Bake control mold 30 min. at 80° C.
11. Cut devices out of flow mold and punch holes with 650 μm diameter punch tool (Technical Innovations #CR0350255N20R4).
12. Clean flow device with transparent tape and align to control mold.
13. Bake 2-layer device for 45 min. at 80° C.
14. While 2-layer device is baking, prepare 20:1 GE RTV A:RTV B (mix 1 min., de-foam 5 min.) to spin on blank silicon wafer.
15. Expose blank(s) to TMCS vapor for 2 min.
16. Spin 20:1 RTV mix on blank wafer(s) at 1600 rpm for 60 s. with a 15 s. ramp.
17. Bake blank wafer for 30 min. at 80° C.
18. Cut out 2-layer device(s) from control mold(s), clean with tape and mount on blank wafer(s). Check for debris and collapsed valves. Collapsed valves can be fixed by applying pneumatic pressure with a syringe to the respective control channel(s). This should overcome valves sticking to channels. Once pressure is applied and released, peel device back from blank wafer and re-mount.
19. Bake 3-layer RTV device(s) for 6-18 hr. Less is best (devices can still handle ~30 psi without delaminating).
20. If output holes need to be punched, do so with technical innovation titanium nitride coated punch (#CR0830655N14R4).
21. Cut 3-layer device(s) out, clean with tape and mount on RCA cleaned glass slide(s).
Check for collapse as in (18).
22. Bake finished devices overnight at 80° C.

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of publication of the same. The invention having now been described by way of written description and example, those of skill in the art will recognize that the invention can be practiced in a variety of embodiments and that the foregoing description and examples are for purposes of illustration and not limitation of the following claims.

The invention claimed is:

1. A microfluidic device comprising two sieve valves and a channel or chamber, wherein a chromatographic separation medium is disposed within the channel or chamber between the sieve valves, thereby forming a separation column, wherein each of said sieve valves is paired with a conventional valve,
   wherein, when actuated, the conventional valve blocks flow of solution past the conventional valve, and
   wherein, when actuated, the sieve valve allows flow of solution but blocks passage of the chromatographic separation medium past the sieve valve.

2. The device of claim 1 that comprises more than 20 separation columns.

3. The device of claim 1 that contains five or more sieve valves paired with conventional valves.

4. The device of claim 1 wherein the sieve valve(s) comprises a membrane that is deflectable into a segment of a microfluidic channel with a substantially rectangular profile and the conventional valve(s) comprises a membrane that is deflectable into a segment of a microfluidic channel with a non-rectangular profile.

5. The device of claim 4 wherein each sieve valve is separated from the conventional valve with which it is paired by no more than 200 microns.

6. The device of claim 4 wherein the chromatographic separation medium comprises a polymeric bead coupled to a ligand.

7. The device of claim 6 wherein the beads have been derivatized to bind a nucleic acid.

8. The device of claim 7 wherein the beads have been derivatized with oligo(dT).

9. The device of claim 6 wherein the beads have been derivatized with a protein.

10. The device of claim 9 wherein the protein is an antibody.

11. A microfluidic device comprising a microfluidic chromatography column, said column comprising a chromatographic separation medium disposed within a channel behind a sieve valve, and optionally disposed between two or more sieve valves, wherein said sieve valve or valves are paired with conventional valves, wherein the sieve valve(s) comprises a membrane that is deflectable into a segment of a microfluidic channel with a non-rounded profile and the conventional valve(s) comprises a membrane that is deflectable into a segment of a microfluidic channel with a rounded profile
   wherein, when actuated, the conventional valve blocks flow of solution past the conventional valve, and
   wherein, when actuated, the sieve valve allows flow of solution but blocks passage of the chromatographic separation medium past the sieve valve.

12. The device of claim 11 wherein the chromatographic separation medium comprises a polymeric bead coupled to a ligand.

13. The device of claim 12 wherein the beads have been derivatized to bind a nucleic acid.

14. The device of claim 13 wherein the beads have been derivatized with oligo(dT).

15. The device of claim 11 wherein the beads have been derivatized with a protein.

16. The device of claim 15 wherein the protein is an antibody.

17. The device of claim 11 wherein each sieve valve is separated from the conventional valve with which it is paired by no more than 200 microns.

18. A microfluidic device comprising at least one sieve valve paired with a conventional valve.

19. The microfluidic device of claim 18 comprising a channel with a non-rounded profile in a first region of the channel and a rounded profile a second region of the channel, and having the sieve valve positioned in the first region and the conventional valve positioned in the second region.

20. The microfluidic device of claim 19 in which the sieve valve and the conventional valve are separated by no more than 200 microns.

* * * * *